United States Patent
Jammikunta

(10) Patent No.: US 9,625,892 B2
(45) Date of Patent: Apr. 18, 2017

(54) SYSTEM AND METHOD FOR MONITORING DEVICE CALIBRATION

(71) Applicant: Honeywell International Inc., Morristown, NJ (US)

(72) Inventor: Ravi Jammikunta, Andhrapradesh (IN)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/739,656

(22) Filed: Jun. 15, 2015

(65) Prior Publication Data

US 2016/0364973 A1 Dec. 15, 2016

(51) Int. Cl.
| | |
|---|---|
| *G08B 21/18* | (2006.01) |
| *G05B 19/00* | (2006.01) |
| *G01D 18/00* | (2006.01) |
| *G01N 27/327* | (2006.01) |
| *A61B 5/1495* | (2006.01) |

(52) U.S. Cl.
CPC ............ *G05B 19/00* (2013.01); *G01D 18/002* (2013.01); *A61B 5/1495* (2013.01); *G01D 18/008* (2013.01); *G01N 27/3274* (2013.01)

(58) Field of Classification Search
CPC ............... G01D 18/002; G01D 18/008; G01N 27/3274; G01N 33/0006; A61B 5/1495
See application file for complete search history.

(56) References Cited

U.S. PATENT DOCUMENTS

| 5,542,294 A * | 8/1996 | Douglas ............... G01M 1/225 73/1.14 |
| 5,594,667 A | 1/1997 | Myers |
| 2009/0082987 A1* | 3/2009 | Collins ............... G01F 25/0007 702/104 |
| 2012/0262298 A1* | 10/2012 | Bohm ............... G01N 27/3274 340/604 |

* cited by examiner

*Primary Examiner* — Hongmin Fan
(74) *Attorney, Agent, or Firm* — Jetter & Associates, P.A.

(57) ABSTRACT

A system and method for monitoring device calibration. The system includes an asset management computer communicatively coupled to field devices. The asset management computer includes a processor connected to a memory device storing a field device drift identifying (FDDI) program. The FDDI program causes the asset management computer to statistically determine at least one process control limit from historical parameter data received from each of the field devices. The system continuously samples current parameter data received from each of the field devices and compares the current parameter data to respective ones of the process control limits for each of the field devices to determine whenever any of the current parameter data is outside the process control limit for identifying a first device drift for a first field device. Responsive to identifying the first device drift, an alert is generated that the first field device needs calibration.

18 Claims, 6 Drawing Sheets

SYSTEM AND METHOD FOR MONITORING DEVICE CALIBRATION

FIELD

Disclosed embodiments relate to computers used with industrial hardware devices, and more specifically relate to monitoring device calibration in an industrial process facility.

BACKGROUND

Process facilities are used in various industries such as petroleum or chemical refining, pharmaceutical, pulp and paper, or other manufacturing operations. Process facilities use process control systems including various field devices to measure and sense process parameters. The field devices can include tank level gauges, temperature sensors, pressure sensors, valve controllers, actuators and other devices. A process facility can use tens or hundreds of field devices to monitor and control the process(es).

Field devices require calibration at regular intervals of time as prescribed by the field device manufacturer in order to maintain accurate measurements and properly function. If a field device is not calibrated, the process data which that device measures may not be accurate which can affect the quality of the process. The calibration of field devices can be performed as scheduled maintenance at time intervals depending on recommendations of field device manufacturers or based on process criticality where that instrument is used.

However, detecting a field device that has gone out of calibration during operation is difficult. The identification of out of calibration measurement values are difficult to identify particularly when the field device is being used in a process.

SUMMARY

This summary is provided to introduce a brief selection of disclosed concepts in a simplified form that are further described below in the Detailed Description including the drawings provided. This Summary is not intended to limit the claimed subject matter's scope.

Disclosed embodiments comprise a method for monitoring device calibration. The method includes providing an asset management computer that is communicatively coupled to a plurality of field devices. The communicably coupled can be wireless, wired such as a cable connecting, or a combination or wired and wireless. The asset management computer includes a processor connected to a memory device having a first non-transitory machine-readable storage medium that stores a field device drift identifying (FDDI) program. The asset management computer is programmed to implement the FDDI program causing the asset management computer to execute for each of the field devices statistically determining at least one process control limit from historical parameter data received from each of the plurality of field devices.

The method further includes continuously sampling current parameter data received from each of the plurality of field devices and comparing the current parameter data to respective ones of the process control limits for each of the field devices to determine whenever any of the current parameter data is outside the process control limit for identifying a first device drift for a first field device of the field devices. As used herein, "continuously sampling" refers to taking the samples with some predefined interval, where the interval period depends on device sampling capability (i.e., at what frequency the device can send the data.) Responsive to identifying the first device drift, an alert (e.g., warning or alarm) is generated that the first field device needs calibration to prompt a calibration be performed.

One disclosed embodiment comprises a system for monitoring device calibration. The system includes an asset management computer communicatively coupled to a plurality of field devices. The asset management computer includes a processor connected to a memory device having a first non-transitory machine-readable storage medium that stores a FDDI program. The asset management computer is programmed to implement the FDDI program causing the asset management computer for each field devices to statistically determine at least one process control limit from historical parameter data received from each of the field devices. The system further continuously samples current parameter data received from each of the field devices and compares the current parameter data to respective ones of the process control limits for each of the field devices to determine whenever any of the current parameter data is outside the process control limit for identifying a first device drift for a first field device of the field devices. Responsive to identifying the first device drift, an alert is generated that the first field device needs calibration.

DETAILED DESCRIPTION

Figure 1:
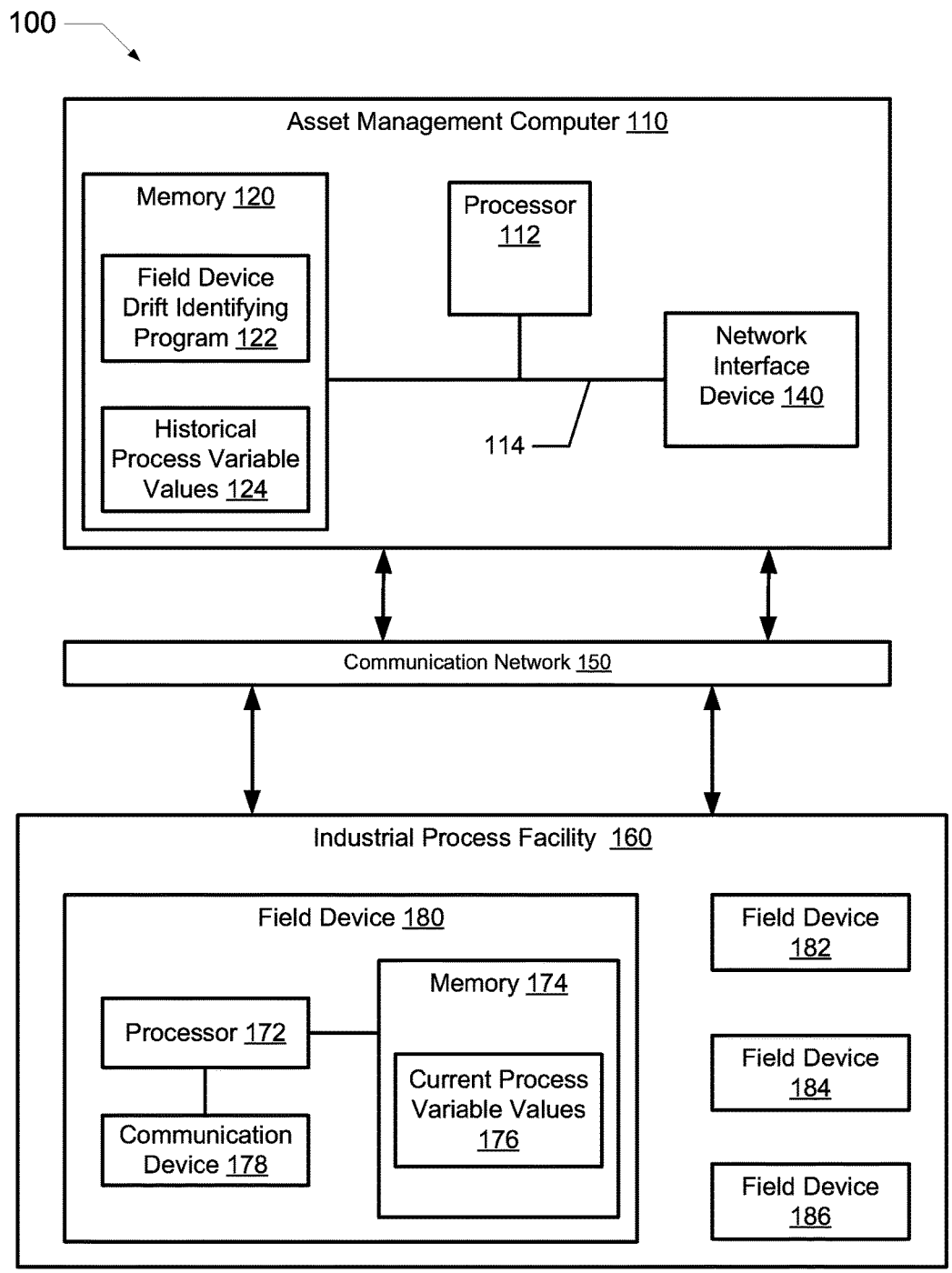
FIG. 1 is a block diagram of an example system for monitoring field device calibration, according to an example embodiment.

Disclosed embodiments are described with reference to the attached figures, wherein like reference numerals are used throughout the figures to designate similar or equivalent elements. The figures are not drawn to scale and they are provided merely to illustrate certain disclosed aspects. Several disclosed aspects are described below with reference to example applications for illustration. It should be understood that numerous specific details, relationships, and methods are set forth to provide a full understanding of the disclosed embodiments.

One having ordinary skill in the relevant art, however, will readily recognize that the subject matter disclosed herein can be practiced without one or more of the specific details or with other methods. In other instances, well-known structures or operations are not shown in detail to avoid obscuring certain aspects. This Disclosure is not limited by the illustrated ordering of acts or events, as some acts may occur in different orders and/or concurrently with other acts or events. Furthermore, not all illustrated acts or events are required to implement a methodology in accordance with the embodiments disclosed herein.

FIG. 1 illustrates a block diagram of an example system 100 for monitoring field device calibration. As shown in FIG. 1, system 100 comprises an asset management computer 110 that is in communication with one or more field devices 180, 182, 184 and 186 (collectively field devices 180-186) located in an industrial process facility (IPF) 160 via a communication network 150.

IPF 160 can be a variety of manufacturing plants or storage locations that handle, process, store and transport a powder, liquid or fluid material. IPF 160 can include manufacturing plants, chemical plants, crude oil refineries, ore processing plants, paper manufacturing plants, water processing plants, electric power generation plants and tank farms. These industries and facilities typically use continuous processes and fluid processing.

Field devices 180-186 are mounted to or are in communication with industrial equipment such as industrial control devices or function as measurement devices within the IPF 160. Field devices 180-186 measure, sense, control and record parameters and movement of materials within IPF 160. For example, field devices 180-186 can measure temperature, pressure and volume. Other field devices 180-186 can control the operation of valves and switches to regulate the flow of fluids or gases.

Asset management computer 110 includes a processor 112 (e.g., digital signal processor (DSP), microprocessor or microcontroller unit (MCU)) having an associated memory 120 that stores a field device drift identifying (FDDI) program 122. Processor 112 can perform any one or more of the monitoring device calibration operations, applications, methods or methodologies described herein. A processor 112 is needed to perform the data processing needed to implement disclosed embodiments because a human cannot monitor, record and perform calculations from process variable data provided essentially continuously being updated on the order of milliseconds as this is clearly too fast for a person to do. Processor 112 is also coupled to a network interface device 140 which facilitates communication with a communication network 150. Processor 112 is coupled to memory 120 and network interface device 140 via a system bus 114.

Memory 120 stores historical process parameters or actual process variable (PV) values 124 that are received from the field devices 180-186 via communication network 150. In one embodiment, historical PV values 124 are received by asset management computer 110 over a period of time and then stored to memory 120 as historical PV values 124. Historical PV values 124 also include a time associated with the measurement of the value by the respective field device 180-186.

Field device 180 is shown including a computing device such as a processor 172 (e.g., digital signal processor (DSP), microprocessor or microcontroller unit (MCU)) having an associated memory 174. Processor 172 is coupled to memory 174. Field devices 180-186 do not need any special programming to implement disclosed embodiments. Processor 172 is also coupled to a communication device 178. Communication device 178 can transmit and receive data via communication network 150. In one embodiment, the communication device 178 can transmit and receive data from communication network 150 via wireless signals. Memory 174 stores current process variable (PV) values 176 that are measured by field device 180 during the operation of IPF 160. In one embodiment, current PV values 176 are tracked and recorded over a period of time and then stored to memory 174.

Processor 112 implements the FDDI program 122 which statistically determines at least one process control limit from the historical PV values 124 received from each of the field devices 180-186. The current PV values 176 or data are generally continuously sampled from each of the field devices 180-186. Continuously sampling is taking samples with some predefined intervals or time period. The interval or time period depends on the device capability of field devices 180-186. The sampling capability depends on how frequently field devices 180-186 can transmit data. The most frequently occurring values which were derived from current PV values 534 are compared to respective ones of the process control limits for each of the field devices to determine whenever any of the most frequently occurring values which were derived from current PV value 534 are outside the process control limit for identifying device drifts for any of the field devices 180-186. For example, responsive to identifying a drift beyond a process control limit for a first field device, an alert is automatically generated that the first field device 180 needs calibration.

By adding intelligence to the asset management computer only field devices which actually require calibration as evidenced by a device drift is attended for maintenance. Setting up calibration based on field device performance as disclosed instead of a conventional fixed scheduled maintenance every several month(s) even though the field device may not have drifted is recognized to be to avoid wasting time and money, and moreover allows carrying out maintenance activities before a conventional schedule maintenance would have the maintenance performed if it drifts before the maintenance interval. However, one can set up calibration based on field device performance as disclosed herein together with a less frequent conventional fixed scheduled maintenance.

Figure 2:
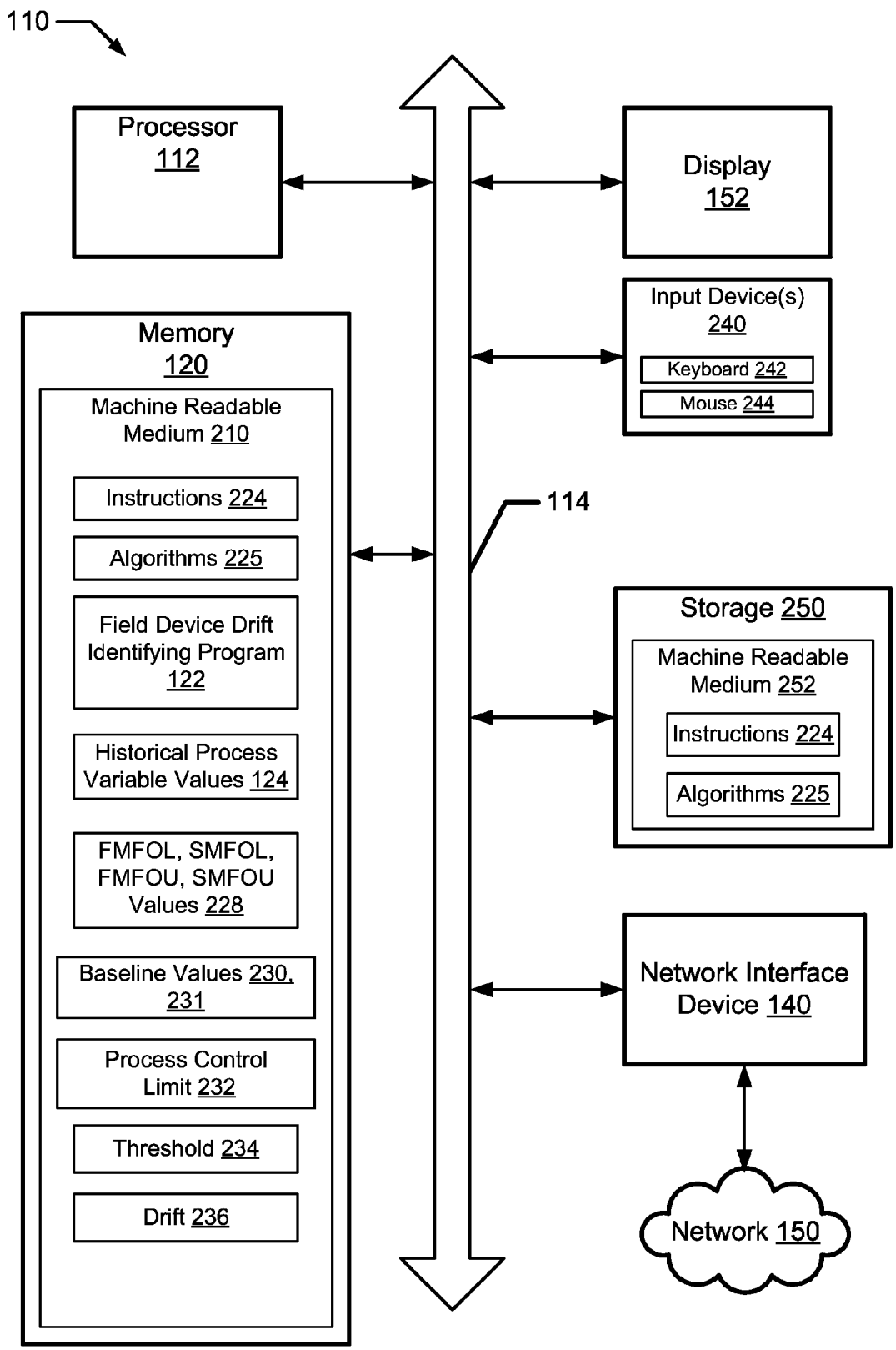
FIG. 2 is a block diagram of an example asset management computer, according to an example embodiment.

FIG. 2 illustrates an example block diagram of asset management computer 110 within which a set of instructions 224 and/or algorithms 225 can be executed causing the asset management computer 110 to perform any one or more of the methods, processes, operations, applications, or methodologies described herein.

Asset management computer 110 includes one or more processors 112 such as a central processing unit (CPU) and a storage device such as memory 120, which communicate with each other via system bus 114 which can represent a data bus and an address bus. Memory 120 includes a machine readable medium 210 on which is stored one or more sets of software such as instructions 224 and/or algorithms 225 embodying any one or more of the methodologies or functions described herein. Memory 120 can store instructions 224 and/or algorithms 225 for execution by processor 112. The asset management computer 110 further includes a display 152 such as a video screen that is connected to system bus 114. The asset management computer 110 also has input devices 240 such as an alphanumeric input device (e.g., keyboard 242) and a cursor control device (e.g., a mouse 244) that are connected to system bus 114.

A storage device 250, such as a hard drive or solid state drive, is connected to and in communication with the system bus 114. The storage device 250 includes a machine readable medium 252 on which is stored one or more sets of software such as instructions 224 and/or algorithms 225 embodying any one or more of the methodologies or functions described herein. The instructions 224 and/or algorithms 225 can also reside, completely or at least partially, within the memory 120 and/or within the processor 112 during execution thereof. The memory 120 and the processor 112 also contain machine readable media.

While the machine readable medium 210 is shown in an example embodiment to be a single medium, the term "machine readable medium" should be taken to include a single medium or multiple media (e.g., a centralized or distributed database, and/or associated caches and servers) that store the one or more sets of instructions. The term "machine readable medium" shall also be taken to include any medium that is capable of storing, encoding or carrying a set of instructions for execution by the computer system and that cause the computer system to perform any one or more of the methodologies shown in the various embodiments of the present invention. The term "machine readable medium" shall accordingly be taken to include, but not be limited to, solid-state memories, optical and magnetic media, and carrier wave signals.

Asset management computer 110 further includes a network interface device 140 that is connected to system bus 114. Network interface device 140 is coupled to communication network 150. Communication network 150 can be a wide variety of communication systems such as hardwired networks including the internet or wireless networks including Wi-Fi or local area networks.

Machine readable medium 210 further stores FDDI program 122. FDDI program 122 when executed by processor 112 monitors the calibration of field devices 180-186 and identifies field devices 180-186 that are out of calibration.

Machine readable medium 210 also stores historical process parameters or process variable (PV) values 124 that are received from field devices 180-186 via communication network 150. In one embodiment, asset management computer 110 receives a plurality of current PV values 176 over a period of time and then stores the received values to historical PV values 124. Historical PV values 124 can also include a time associated with the measurement of the value by the respective field device 180-186.

Machine readable medium 210 further stores a first most frequently occurring lower (FMFOL) value, a first most frequently occurring upper (FMFOU) value, a second most frequently occurring lower (SMFOL) value and a second most frequently occurring upper (SMFOU) value (most frequently occurring values) 228. The FMFOL and FMFOU values are based on historical PV values 124 from a first time period. The SMFOL and SMFOU values are based on historical PV values 124 from a second time period. Machine readable medium 210 further stores not only first and second, but all 'n' number of intervals related to the most frequently occurring values.

Machine readable medium 210 also stores a baseline most frequently occurring lower (BMFOL) value and a baseline most frequently occurring upper (BMFOU) value (baseline values) 230. The BMFOL value is determined based on the based on the FMFOL value, the SMFOL value and on additional most frequently occurring lower values from later time periods. The BMFOU value is determined based on the based on the FMFOU value, the SMFOU value and on additional most frequently occurring upper values from later time periods.

Machine readable medium 210 also stores process control limit 232, threshold 234 and drift 236. Process control limit 232 is at least one of the baseline values 230. If a device has upper and lower side values then the control limit will have two baseline values. If a device has only one side values then there will be only one baseline value. In one embodiment, threshold 234 is a pre-determined value of deviation between the most frequently occurring values which were derived from current PV values 534 and the process control limit 232. In another embodiment, a drift 236 (in percent) can be calculated based on the ratio of most frequently occurring values which were derived from current PV values 176 to process control limit 232. If the deviation is greater than threshold 234 or if the drift is greater than a pre-determined value, the associated field device is identified as needing calibration.

Figure 3:
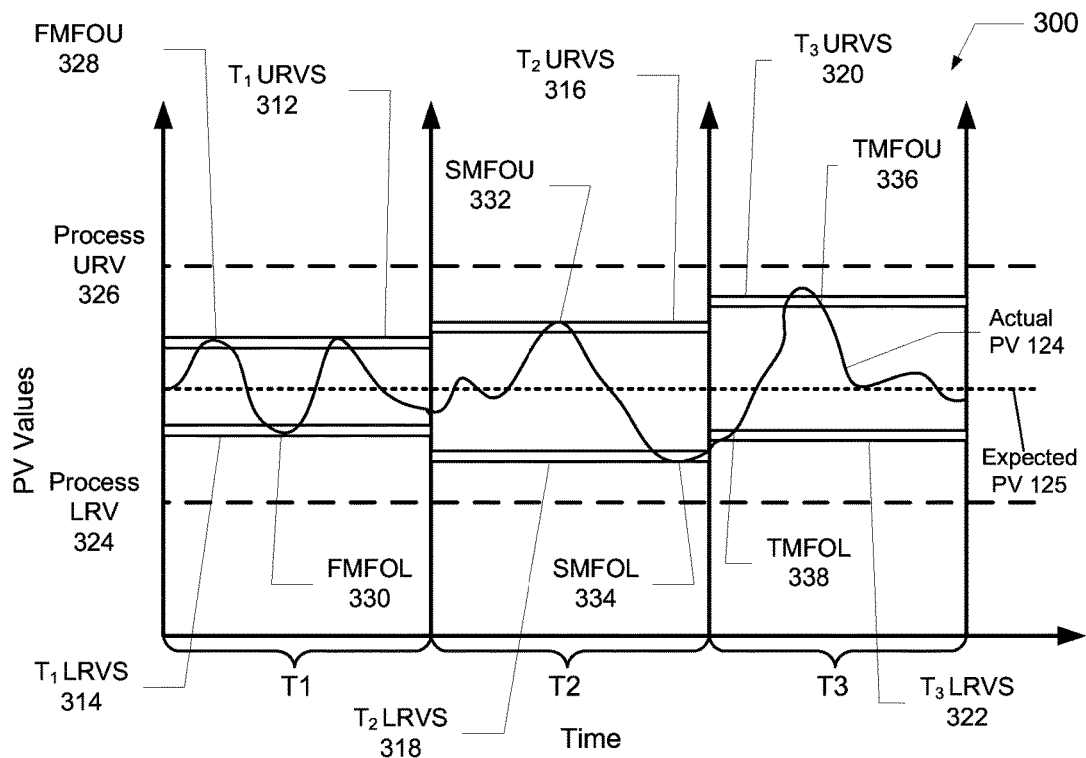
FIG. 3 is an example graph of process values versus time for several time periods, according to an example embodiment.

FIG. 3 illustrates a graph 300 of historical or actual PV values 124 versus time for several time periods shown as time periods T1, T2 and T3. While only three time periods are shown, graph 300 can include more time periods, such as tens of thousands of time periods. The historical PV values 124 will typically not be constant over time and will vary. FDDI program 122 executing on processor 112 can plot graph 300 over time and can statistically calculate or determine upper range values set (URVS) 312 and lower range value set (LRVS) 314. URVS 312 is the highest values set of the historical PV values 124 in a certain time interval. LRVS 314 is the lowest values set of the historical PV values 124 in a certain time interval.

FDDI program 122 executing on processor 112 can plot graph 300 and can take samples of PV values and determines URVS based on the most frequently occurring highest PV values in time periods T1 to Tn and determine the FMFOU value 328 in time period T1, the SMFOU value 332 in time period T2 and the third most frequently occurring upper (TMFOU) value 336 in time period T3. Processor 112 executing FDDI program 122 also can take samples of PV values and determines LRVS based on the most frequently occurring lowest PV values in time periods T1 to Tn and determine the FMFOL value 330 in time period T1, the SMFOL value 334 in time period T2 and the third most frequently occurring lower (TMFOL) value 338 in time period T3. FMFOU, SMFOU, TMFOU can be determined by finding the most frequent occurring upper value in URVS or the just highest value in URVS in that time interval. This depends on device type, process type and required accuracy levels. Similarly FMFOL,SMFOL,TMFOL will be determined by finding the most frequent occurring lower value in LRVS or the just lowest value in LRVS in that time interval. This also depends on device type, process type and required accuracy levels. This operation will continue for all 'n' sample intervals. These most frequently occurring highest and lowest values can be determined by plotting the histogram of PV values in that interval T.

FDDI 122 executing on processor 112 divides the 'n' samples interval times into 's' number of sets. For each set, the most frequently occurring upper value and lower value will be calculated. These sample number 'n' and set count 's' will be configured based on the process type, device type and required accuracy levels.

Figure 4:
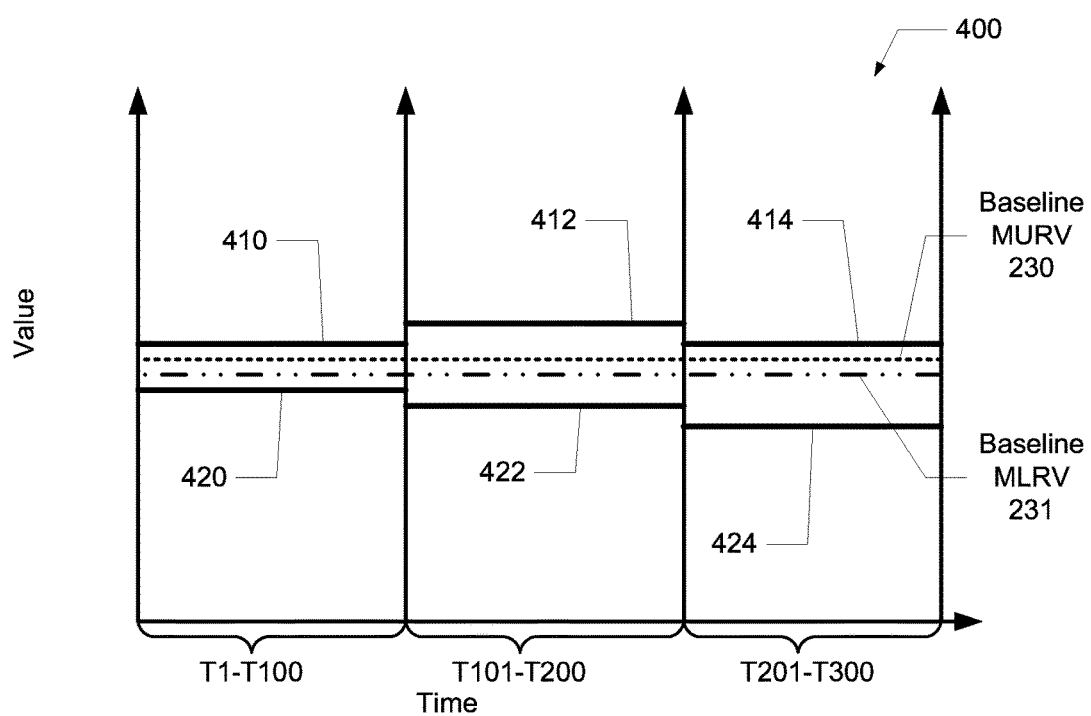
FIG. 4 is an example graph of process values versus time for several time periods, according to an example embodiment.

FIG. 4 is an example graph 400 of historical PV values 124 versus time for several time periods such as time periods T1-T100, T101-T200 and T201-T300. In this example, 'n' is 300 and 's' is 3. This means the total number of sample intervals 'n' are 300 and the number of sets 's' are 3. FDDI program 122 executing on processor 112 can plot graph 400 and can statistically determine the most frequently occurring upper value (MURV) and the most frequently occurring lower value (MLRV) in intervals of each set. This MURV can be calculated by plotting the histogram of FMFOU, SMFOU, TMFOU . . . sMFOU of each set. Similarly MLRV will be calculated by plotting the histogram of FMFOL, SMFOL, TMFOL . . . sMFOL for each set. Here sMFOU and sMFOL are last sample interval values in that set. These operations may include some other statistical methods also for more accuracy. Processor 112 can determine the MURV 410 in time periods T1-T100, the MURV 412 in time periods T101-T200 and the MURV 414 in time periods T201-T300. Processor 112 can determine the MLRV 420 in time periods T1-T100, the MLRV 422 in time periods T101-T200 and the MLRV 424 in time periods T201-T300. Here these time periods are shown as "n" equal to 300 just for illustration. This will generally be decided based on the process type and accuracy levels. These sets "s" of time intervals can also be decided based on process type, accuracy levels, device type.

Processor 112 executing FDDI program 122 can determine baseline values 230 and 231. Baseline MURV 230 is the average of MURVs 410, 412 and 414. Baseline MLRV 231 is the average of MLRVs 420, 422 and 424. Determining the baseline values is the BASELINE phase. This procedure is used in the initial phase of calibrating a device or a after a new device is installed in the process, and the baseline data will be stored in a database in memory 120 for future reference. The second phase is the PRACTISING phase. In this phase, current PV values 176 will be read from the device and all the same BASELINE phase steps need to be followed for this phase also to determine the MURV/MLRV for T1-Tn. These new MURV/MLRV will be compared with the baseline MURV/MLRV values in order to determine if any of the field devices 180-186 are out of calibration and need to be calibrated.

Figure 5A:
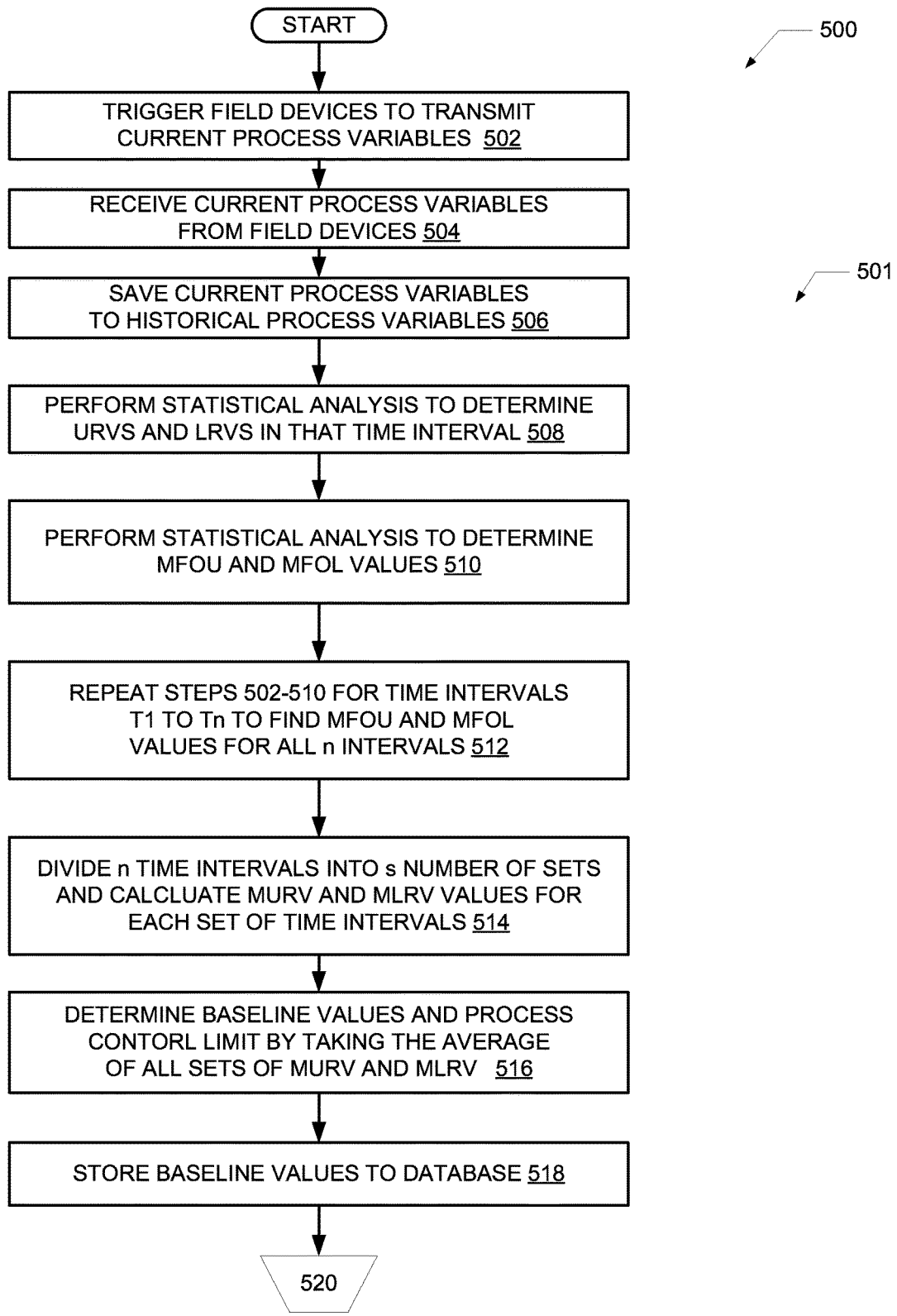
FIGS. 5A-C are flow charts that shows steps in an example method of monitoring field device calibration, according to an example embodiment.
Figure 5B:
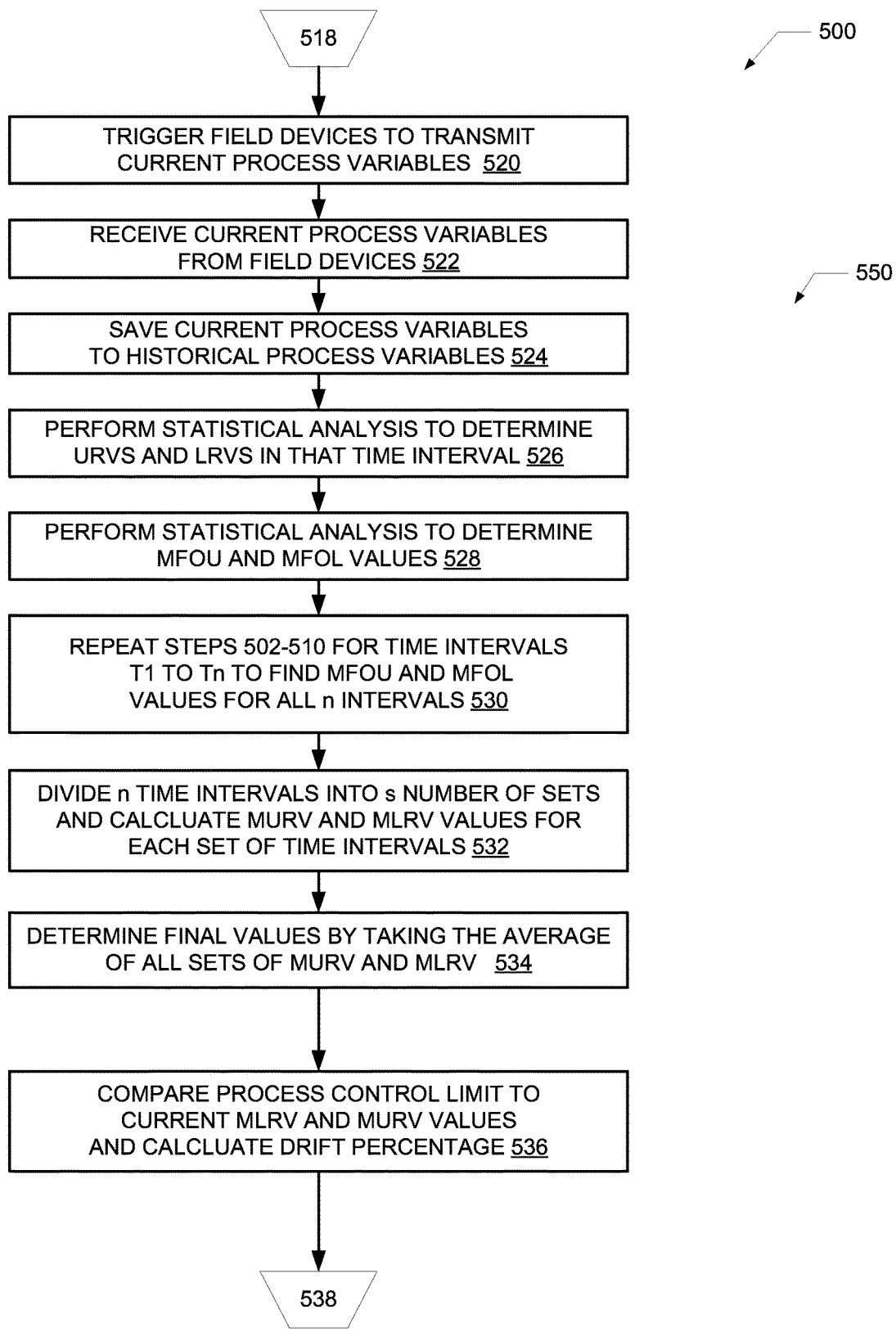
Figure 5C:
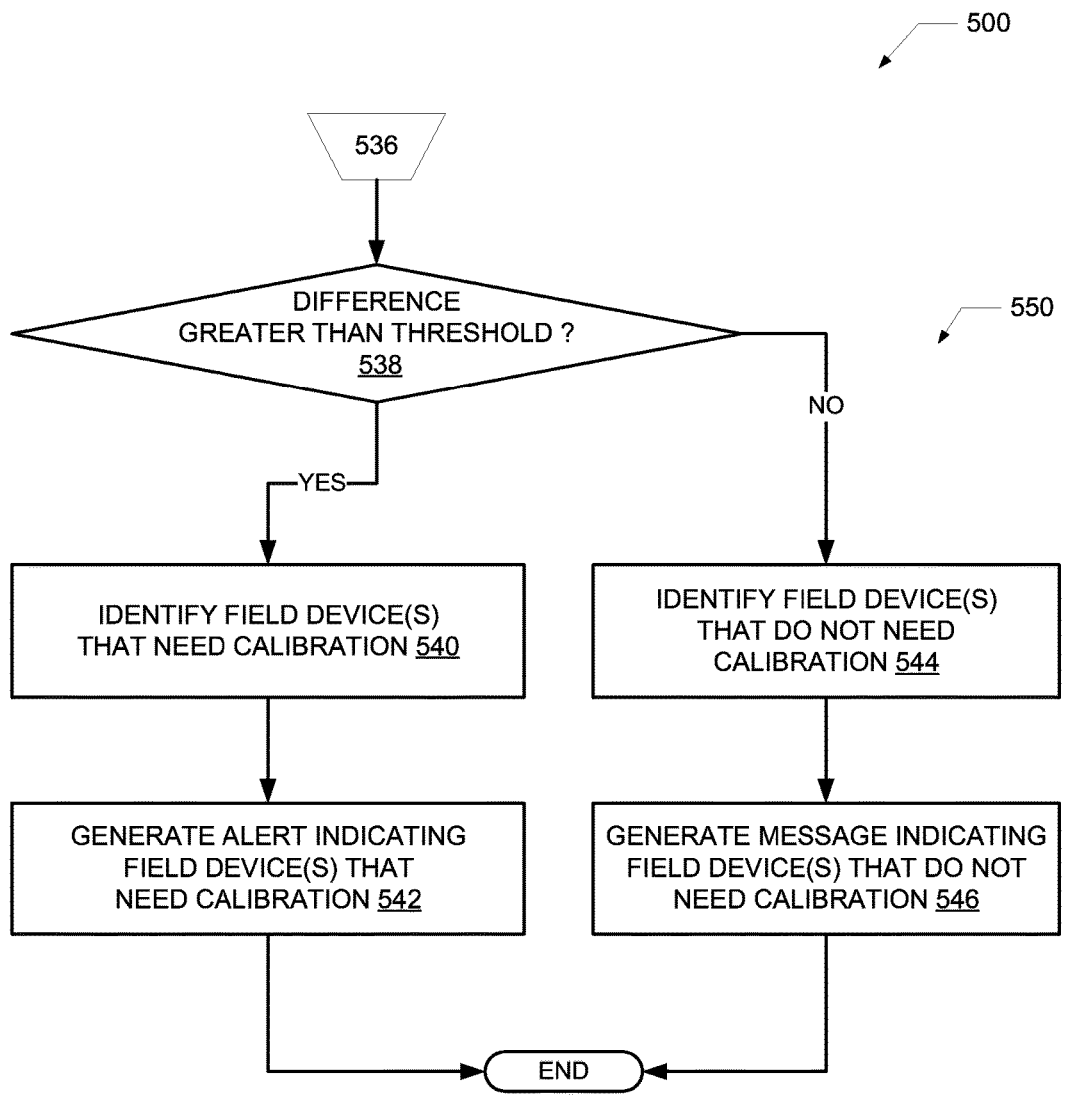

FIGS. 5A-C are flow charts showing steps in an example method 500 for monitoring device calibration using system 100. With reference to FIGS. 1-4, method 500 can be implemented via the execution of instructions 224 and/or algorithms 225 by processor 112 within asset management computer 110 and specifically by the execution of FDDI program 122 by processor 112. FIG. 5A illustrates the BASELINE phase 501 and FIGS. 5B and 5C illustrate the PRACTISING phase 550.

The BASELINE phase 501 of method 500 begins at the start block and proceeds to block 502. At block 502, processor 112 triggers field devices 180-186 to transmit current PV values 176 from field device 180 and also to transmit current PV values from field devices 182-186. Field device 180 transmits current PV values 176 for one or more time periods to asset management computer 110 via communication device 178, network 150 and network interface device 140. In one embodiment, field device 180 can continuously (e.g., every 100 msec) transmit current PV values 176 to asset management computer 110. Processor 112 receives the current PV values 176 from field device 180 (block 504) and saves the current PV values to historical PV values 124 over several time periods (block 506).

Processor 112 determines an upper range values set (URVS) 312 and a lower range values set (LRVS) 314 (block 508) for each time interval. URVS 312 is the set of highest values of the historical PV values 124 in a certain time interval which are greater than expected PV value 125. LRVS 314 is the set of lowest values of the historical PV values 124 in a certain time interval which are lesser than expected PV value 125.

At block 510, processor 112 takes samples from URVS 312 in time periods T1 and determines the FMFOU value 328 in time period T1. This can be direct highest PV value in URVS or the most frequent occurring highest value in URVS. Processor 112 also takes the samples LRVS 314 in time periods T1 and determines the FMFOL value 330 in time period T1. This can be direct lowest PV value in LRVS or most frequently occurring lowest PV value in LRVS.

At block 512, processor 112 performs the same operation which was carried out for T1 will be carried out for all 'n' samples. Processor 112 takes the samples from URVS 312 and determines SMFOU value 332 in time period T2 and TMFOU value 336 in time period T3 and any additional MFOU values in additional time periods. Processor 112 takes the samples from LRVS 314 and determines SMFOL value 334 in time period T2 and TMFOL value 338 in time period T3 and any additional MFOL values in additional time periods.

At block 514, processor 112 divides the 'n' time interval samples into 's' number of sets. For each set, the most frequently occurring upper value (MURV) and the most frequently occurring lower value (MLRV) will be calculated by plotting the histogram of most frequently occurring upper values and most frequently occurring lower values of each samples in that set. Processor 112 determines baseline values 230 and 231 (block 516). Baseline MURV 230 will be calculated by taking the average of all sets MURVs and MLRVs. For example, baseline MURV 230 is the average of MURVs 410, 412 and 414. Baseline MLRV 231 is the average of MLRVs 420, 422 and 424. After determining the baseline values 230 and 231, processor 112 selects one or more of baseline values 230 and/or 231 as process control limit 232. At block 518, baseline MURV 230, baseline MLRV 231 and process control limit 232 are stored to memory 120 and storage device 250.

The PRACTISING phase 550 (FIG. 5B) of method 500 begins at block 520. In this second phase, the same steps of blocks 502 to 516 are repeated as blocks 520 to 534 for the current PV values 176 which are now being received from field devices 182-186. In block 534 processor 112 will determine average MLRV and average MURV for the current PV values. At block 536, processor 112 performs a comparison between the new average MLRV and the stored base lined MLRV 231, and the deviation percentage will be calculated. Similarly comparison between new average MURV and the stored base lined MURV 230 will be performed and the deviation percentage is also calculated.

Turning to FIG. 5C, at decision block 538, processor 112 determines the difference between the process control limit 232 and the new average MURV and new average MLRV. If the new average MURV or new average MLRV are beyond the threshold 234 then that device will be identified for calibration. Threshold 234 is a pre-determined value to identify the deviation between base lined values 230, 231 and new average MURV and average MLRV. Drift 236 is calculated based on the ratio of new average MURV and average MLRV to process control limit 232. If the deviation is greater than threshold 234 or if the drift is greater than a pre-determined value, the associated field device is identified as needing calibration.

In response to the difference between the process control limit 232 and new average MURV and average MLRV being beyond the threshold 234 or drift 236, processor 112 identifies the respective field devices 180-186 that need calibration (block 540). In response to the difference between the process control limit 232 and the new average MURV and average MLRV being less than threshold 234 or drift 236, processor 112 identifies the respective field devices 180-186 that do not need calibration (block 544). Processor 112 generates an alert (e.g., warning or alarm) indicating to a user the field devices that need calibration (block 542) and generates a message indicating to a user the field devices that do not need calibration (block 546). Processor 112 can show the alert and message to the user via display 152. Method 500 then ends.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

As will be appreciated by one skilled in the art, the subject matter disclosed herein may be embodied as a system, method or computer program product. Accordingly, this Disclosure can take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, this Disclosure may take the form of a computer program product embodied in any tangible medium of expression having computer usable program code embodied in the medium.

Any combination of one or more computer usable or computer-readable medium(s) may be utilized. The computer-usable or computer-readable medium may be, for example, but not limited to, an electronic, magnetic, optical, electromagnetic, infrared, or semiconductor system, apparatus, or device. More specific examples (a non-exhaustive list) of the computer-readable medium would include non-transitory media including the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CDROM), an optical storage device, or a magnetic storage device.

The invention claimed is:

1. A method for monitoring device calibration, comprising:
providing an asset management computer communicatively coupled to a plurality of field devices in an industrial facility said asset management computer including a processor connected to a memory device having a first non-transitory machine-readable storage medium storing a field device drift identifying (FDDI) program, wherein said asset management computer is programmed to implement said FDDI program to cause said asset management computer to execute for each of said plurality of field devices:
statistically determining at least one process control limit from historical parameter data received from each of said plurality of field devices, said process control limit based on at least one of a frequently occurring lower value and a frequently occurring upper value;
continuously sampling current parameter data received from each of said plurality of field devices;
comparing said current parameter data to respective ones of said process control limits for each of said plurality of field devices to determine whenever any of said current parameter data is outside said process control limit for identifying a first device drift for a first field device of said plurality of field devices, and
responsive to identifying said first device drift, generating an alert that said first field device needs calibration.

2. The method of claim 1, wherein said historical parameter data comprises a plurality of first time period process variable (PV) values from respective said field devices and a plurality of second time period process variable (PV) values from respective said field devices.

3. The method of claim 2, wherein said asset management computer further executes:
receiving said first time period PV values and said second time period PV values from said plurality of field devices;
storing said first time period PV values and said second time period PV values to said memory device.

4. The method of claim 2, wherein said asset management computer further executes:
determining at least one first most frequently occurring lower (FMFOL) value and at least one first most frequently occurring upper (FMFOU) value based on said first time period PV values; and
determining at least one second most frequently occurring lower (SMFOL) value and at least one second most frequently occurring upper (SMFOU) value based on said second time period PV values.

5. The method of claim 4, wherein said asset management computer further executes:
determining a baseline most frequently occurring lower (BMFOL) value based on said FMFOL value and said SMFOL value; and
determining a baseline most frequently occurring upper (BMFOU) value based on said FMFOU value and said SMFOU value.

6. The method of claim 5, wherein said process control limit is at least one of said BMFOL value or said BMFOU value.

7. The method of claim 5, wherein said asset management computer further executes:
storing said BMFOL value and said BMFOU value to said memory device.

8. The method of claim 5, wherein identifying said first device drift for said first field device includes said asset management computer further executing:
comparing said current parameter data to said BMFOL value and to said BMFOU value; and
in response to the deviation between said current parameter data and said BMFOL value or said BMFOU value being greater than a threshold, identifying said first device drift for said first field device.

9. The method of claim 1, wherein said asset management computer further executes:
responsive to not identifying said first device drift, generating a message that said first field device does not need calibration.

10. A system for monitoring device calibration, comprising:
an asset management computer communicatively coupled to a plurality of field devices, said asset management computer including a processor connected to a memory device having a first non-transitory machine-readable storage medium storing a field device drift identifying (FDDI) program, wherein said asset management computer is programmed to implement said FDDI program causing said asset management computer for each of said plurality of field devices to:
statistically determining at least one process control limit from historical parameter data received from each of said plurality of field devices, said process control limit based on at least one of a frequently occurring lower value and a frequently occurring upper value;
continuously sampling current parameter data received from each of said plurality of field devices;
comparing said current parameter data to respective ones of said process control limits for each of said plurality of field devices to determine whenever any of said current parameter data is outside said process control limit for identifying a first device drift for a first field device of said plurality of field devices, and responsive to identifying said first device drift, generating an alert that said first field device needs calibration.

11. The system of claim 10 wherein said historical parameter data comprises a plurality of first time period process variable (PV) values from respective said field devices and a plurality of second time period process variable (PV) values from respective said field devices.

12. The system of claim 11 wherein said FDDI program further causes said asset management computer to:
receive said first time period PV values and said second time period PV values from said plurality of field devices;
store said first time period PV values and said second time period PV values to said memory device.

13. The system of claim 11 wherein said FDDI program further causes said asset management computer to:
determine at least one first most frequently occurring lower (FMFOL) value and at least one first most frequently occurring upper (FMFOU) value based on said first time period PV values; and
determine at least one second most frequently occurring lower (SMFOL) value and at least one second most frequently occurring upper (SMFOU) value based on said second time period PV values.

14. The system of claim 13 wherein said FDDI program further causes said asset management computer to:
determine a baseline most frequently occurring lower (BMFOL) value based on said FMFOL value and said SMFOL value; and
determine a baseline most frequently occurring upper (BMFOU) value based on said FMFOU value and said SMFOU value.

15. The system of claim 14 wherein said process control limit is at least one of said BMFOL value or said BMFOU value.

16. The system of claim 14 wherein said FDDI program further causes said asset management computer to:
store said BMFOL value and said BMFOU value to said memory device.

17. The system of claim 14 wherein identifying said first device drift for said first field device includes said FDDI program further causing said asset management computer to:
compare said current parameter data to said BMFOL value and to said BMFOU value; and
in response to the deviation between said current parameter data and said BMFOL value or said BMFOU value being greater than a threshold, identify said first device drift for said first field device.

18. The system of claim 10 wherein said FDDI program further causes said asset management computer to:
responsive to not identifying said first device drift, generate a message that said first field device does not need calibration.

* * * * *